United States Patent [19]
Brightwell et al.

[11] Patent Number: 5,723,464
[45] Date of Patent: Mar. 3, 1998

[54] PIPERAZINE DERIVATIVES

[75] Inventors: Christopher Ian Brightwell, Windsor; Michael Gerard Kelly, Maidenhead, both of Great Britain

[73] Assignee: American Home Products Corporation, Madison, N.J.

[21] Appl. No.: 459,205

[22] Filed: Jun. 2, 1995

[30] Foreign Application Priority Data

Jun. 3, 1994 [GB] United Kingdom ............... 9411099

[51] Int. Cl.$^6$ ................. A61K 31/495; C07D 401/14
[52] U.S. Cl. ................. 514/254; 544/364; 544/373
[58] Field of Search ............... 544/364; 514/254

[56] References Cited

U.S. PATENT DOCUMENTS 4,988,814  1/1991  Abou-Garbia ............... 544/295

FOREIGN PATENT DOCUMENTS

| | | |
|---|---|---|
| 0395312 | 10/1990 | European Pat. Off. |
| 0512755 | 11/1992 | European Pat. Off. |
| 92/06082 | 4/1992 | WIPO |
| 93/21179 | 10/1993 | WIPO |
| 94/15919 | 7/1994 | WIPO |

OTHER PUBLICATIONS

A. Fletcher et al., T.I.P.S. 14, 441–448 (1993).
Hoyer et al., Brit. J. Pharmacol. 1992, 105 29P.
Millan et al, *Journal of Pharmacology and Experimental Therapeutics*, vol. 262, pp. 451–463 (1992).

Primary Examiner—Emily Bernhardt
Attorney, Agent, or Firm—R. F. Boswell, Jr.

[57] ABSTRACT

Compounds are disclosed which have the general formula A:

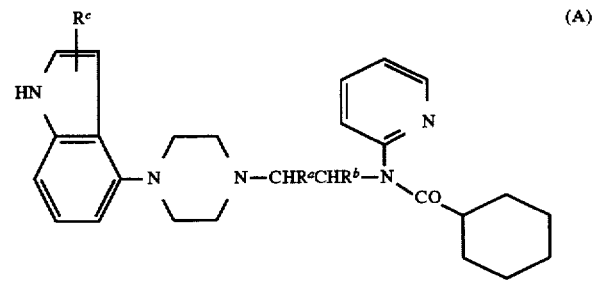

where $R^a$ and $R^b$ are each hydrogen or methyl and $R^c$ is hydrogen, halo or $C_{1-4}$ alkyl optionally in the form of a pharmaceutically acceptable acid addition salt. The compounds are useful in the treatment of CNS disorders.

13 Claims, No Drawings

PIPERAZINE DERIVATIVES

This invention relates to novel piperazine derivatives, to processes for their preparation, to their use and to pharmaceutical compositions containing them. The novel compounds are useful as 5-$HT_{1A}$ binding agents, particularly as 5-$HT_{1A}$-antagonists.

EP-A-0512755 discloses compounds of the general formula

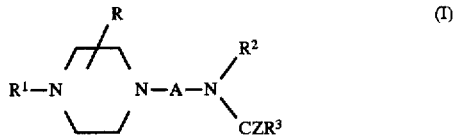

and the pharmaceutically acceptable acid addition salts thereof wherein

A is an alkylene chain of 2 to 4 carbon atoms optionally substituted by one or more lower alkyl groups, Z is oxygen or sulphur, R is hydrogen or lower alkyl, $R^1$ is a mono or bicyclic aryl or heteroaryl radical, $R^2$ is a mono or bicyclic heteroaryl radical and $R^3$ is hydrogen, lower alkyl, cycloalkyl, cycloalkenyl, cycloalkyl(lower)alkyl, aryl, aryl(lower)alkyl, heteroaryl, heteroaryl(lower)alkyl, a group of formula —$NR^4R^5$ [where $R^4$ is hydrogen, lower alkyl, aryl or aryl(lower)alkyl and $R^5$ is hydrogen, lower alkyl, —CO(lower)alkyl, aryl, COaryl, aryl(lower)alkyl, cycloalkyl, or cycloalkyl-(lower)alkyl or $R^4$ and $R^5$ together with the nitrogen atom to which they are both attached represent a saturated heterocyclic ring which may contain a further hetero atom] or a group of formula $OR^6$ [where $R^6$ is lower alkyl, cycloalkyl, cycloalkyl(lower) alkyl, aryl, aryl(lower)alkyl, heteroaryl or heteroaryl(lower) alkyl].

The compounds are disclosed as 5-$HT_{1A}$ binding agents, particularly 5-$HT_{1A}$ antagonists, e.g. for the treatment of CNS disorders, for example anxiety.

We have now found that a small group of compounds falling within formula (I), but not specifically disclosed in EP-A-0512755, have specially advantageous properties that made them particularly useful as 5-$HT_{1A}$ antagonists in the treatment of CNS disorders when administered by the oral route.

The novel compounds of the invention are compounds of the general formula

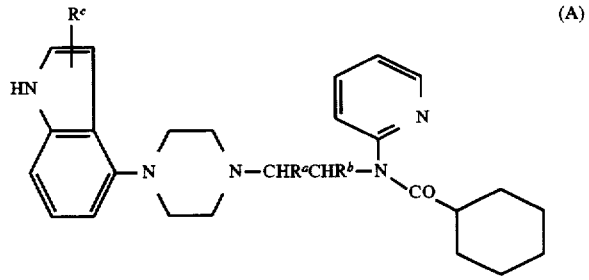

where $R^a$ and $R^b$ are each hydrogen or methyl and $R^c$ is hydrogen, halo or C1–4 alkyl (preferably hydrogen or methyl) and the pharmaceutically acceptable acid addition salts thereof.

Examples of the novel compounds of the invention are (A1). (R)-N-(1-methyl-2-(4-indolyl-1-piperazinyl)ethyl)-N-(2-pyridyl)-cyclohexanecarboxamide (A2). (R)-N-(2-methyl-2-(4-indolyl-1-piperazinyl)ethyl)-N-(2-pyridyl)-cyclohexanecarboxamide (A3). N-(2-[4-(4-indolyl-1-piperazinyl]ethyl]-N-(2-pyridyl)cyclohexanecarboxamide and their pharmaceutically acceptable acid addition salts.

We have found that the novel compounds of the present invention are potent 5-$HT_{1A}$ binding agents, being similar to potency to the most potent of the compounds disclosed in EP-A-0512755. The novel compounds selectively bind to the 5-$HT_{1A}$ receptors and the selectivity of the novel compounds (i.e. the binding affinity of the compounds at the 5-$HT_{1A}$ receptors compound to their binding affinity at the $\alpha_1$ receptors) is at least comparable with the most selective of the compounds disclosed in EP-A-0512755. The novel compounds are 5-$HT_{1A}$ antagonists when tested by standard pharmacological procedures. Surprisingly we have found that the novel compounds are particularly potent as 5-$HT_{1A}$ antagonists when administered by the oral route. The novel compounds are many more times more potent, as 5-$HT_{1A}$ antagonists, when administered by the oral route, than the most potent compounds of EP-A-512755. The 5-$HT_{1A}$ antagonists of the present invention can be used for the treatment of CNS disorders, such as schizophrenia (and other psychotic disorders such as paranoia and manodepressive illness) and anxiety (e.g. generalised anxiety disorders, panic attacks and obsessive compulsive disorders), in mammals, particularly humans. The 5-$HT_{1A}$-antagonists can also be used as antidepressants, hypotensives and as agents for regulating the sleep/wake cycle, feeding behaviour and/or sexual function and as cognition enhancing agents. The increased oral bioavailability of the novel compounds of the invention, compared to that of the class of compounds disclosed in EP-A-512755 is particularly advantageous in that a much smaller dose of compound can be administered orally to produce a similar therapeutic effect.

Tables I and II below summarise the 5-$HT_{1A}$ receptor binding activity, the $\alpha_1$ receptor binding activity, the binding selectivity (i.e. the ratio of 5-$HT_{1A}$ binding to ($\alpha_1$-binding) and the 5-$HT_{1A}$ antagonist activity by the oral route of the compounds disclosed in EP-A-512755 and the novel compounds of the present invention.

TABLE I

| 1<br>Compounds of prior art (Example No of EP-0512755) | 2<br>5$HT_{1A}$ binding $IC_{50}$ (nM) | 3<br>$\alpha_1$ binding $IC_{50}$ (nM) | 4<br>Ratio 5$HT_{1A}$/$\alpha_1$ | 5<br>5-$HT_{1A}$-antagonist activity MED mg/kg po | 6<br>5-$HT_{1A}$-antagonist Ratio ($ED_{50}$ antagonist @ 3mg/kg po)/$ED_{50}$ vehicle |
|---|---|---|---|---|---|
| 3 | 2.2 | 230 | 105 | 1 | 4.2 |
| 5 | 12 | 230 | 19.2 | >10 | |
| 6 | 60 | 245 | 4 | | |
| 8 | 90 | 140 | 2.5 | | |
| 11 | 1 | 197 | 197 | 10 | |
| 17 | 3.1 | 63 | 19.3 | 1 | 7.6 |
| 20 | 4.1 | 385 | 93.9 | >10 | |
| 30 | 14 | 74 | 5.3 | 10 | |
| 33 | 1.4 | 125 | 89.3 | 10 | 7.0 |
| 46 | 2.3 | 798 | 346.9 | 3 | |
| 47 | 4.9 | 64 | 13 | 3–10 | |
| 48 | 6.4 | 126 | 19.7 | | |
| 49 | 2.7 | 1403 | 519.6 | 10 | |
| 50 | 4 | 40 | 10 | | |
| 51 | 3.7 | 46 | 12.4 | <10 | |
| 52 | 147 | | | | |
| 53 | 8 | 558 | 69.8 | 10 | |
| 54 | 175 | | | | |
| 55 | 2.3 | 688 | 299.1 | 1 | 3.2 |
| 56 | 2.7 | 56 | 20.7 | | |
| 57 | 12.7 | 281 | 22.1 | | |
| 58 | 16 | 28 | 1.75 | 1–3 | |

TABLE I-continued

| 1<br>Compounds of prior art (Example No of EP-0512755) | 2<br>5HT$_{1A}$ binding IC$_{50}$ (nM) | 3<br>α$_1$ binding IC$_{50}$ (nM) | 4<br>Ratio 5HT$_{1A}$/α1 | 5<br>5-HT$_{1A}$- antagonist activity MED mg/kg po | 6<br>5-HT$_{1A}$- antagonist Ratio (ED$_{50}$ antagonist @ 3mg/kg po)/ED$_{50}$ vehicle |
|---|---|---|---|---|---|
| 59 | 67 | | | | |
| 60 | 3 | 312 | 104 | 0.3 | 7.4 |
| 61 | 18 | 136 | 7.1 | | |
| 62 | 10 | 144 | 14.4 | | |
| 63 | 131 | | | | |
| 64 | 35 | | | | |
| 65 | 13 | 115 | 8.8 | | |
| 66 | 1.8 | 28 | 15.5 | | |

TABLE II

| 1<br>Compounds of the invention | 2<br>5HT$_{1A}$ binding IC$_{50}$ (nM) | 3<br>α$_1$ binding IC$_{50}$ (nM) | 4<br>Ratio 5HT$_{1A}$/α1 | 5<br>5-HT$_{1A}$- antagonist activity MED mg/kg po | 6<br>5-HT$_{1A}$- antagonist Ratio (ED$_{50}$ antagonist @ 3mg/kg po)/ED$_{50}$ vehicle |
|---|---|---|---|---|---|
| A1 | 4.3 | 2427 | 564.4 | 0.3 | 33.5 |
| A2 | 6.8 | 969 | 142.5 | 0.3 | 23.4 |
| A3 | 3.2 | 1016 | 317.5 | 1 | 34.4 |

The compounds were tested for 5-HT$_{1A}$ binding affinity (column 2) in rat hippocampal membrane homogenate by the method of B. S. Alexander and M. D. Wood, J. Pharm. Pharmacol., 1988, 40, 888–891.

The compounds were tested for α$_1$ binding affinity (column 3) by the procedure of A. L. Marrow et al. Mol. Pharmacol., 1986, 29, 321.

5-HT$_{1A}$ receptor antagonist activity (columns 5 and 6) is assessed by the ability of the selective 5-HT$_{1A}$ receptor agonist, 8-OH-DPAT, to induce the '8-OH-DPAT syndrome' in rats characterised by extended flat body posture, forepaw treading and hyperlocomotion. The 8-OH-DPAT syndrome is scored as present (definite syndrome response) or absent (equivocal or no syndrome response) during the period 0–5 min following intravenous (i.v.) administration of the test agonist via a lateral tail vein.

A range of doses, on a logarithmic scale and encompassing the expected ED$_{50}$, were chosen for the test agonist following preliminary evaluation. The first animal received a dose of the test agonist approximating the expected ED$_{50}$. If the animal responded (syndrome present) the subsequent animal received the next lowest dose on the scale, whereas if the animal did not respond (syndrome absent or equivocal) the next animal received the next highest dose of the chosen scale. This procedure was repeated for a minimum of 10 animals, with animals being tested sequentially.

Test antagonists were administered orally (p.o.) 60 min. before i.v. administration of 8-OH-DPAT. ED$_{50}$ values for 8-OH-DPAT were determined for the different pretreatment groups using the sequential up/down procedure as described above.

Minimum effective doses (MEDs) are taken as the lowest dose tested at which confidence limits for the ED$_{50}$ values for the antagonist and vehicle pretreated groups do not overlap.

The response to the selective 5-HT$_{1A}$ receptor agonist, 8-OH-DPAT, is represented as an ED$_{50}$ value for induction of the 8-OH-DPAT syndrome, which is determined using the sequential up/down analysis following intravenous administration. 5-HT$_{1A}$ antagonist activity is determined by the ability of the test compound to antagonise the response to 8-OH-DPAT, i.e. to increase the ED$_{50}$ for induction of the 8-OH-DPAT syndrome compared with vehicle pretreatment. The ratios represent the ED$_{50}$ value for 8-OH-DPAT following pretreatment with the test compound at 3 mg/kg p.o. (ED$_{50}$ antagonist) divided by the ED$_{50}$ value for 8-OH-DPAT following pretreatment with vehicle (ED$_{50}$ vehicle).

i.e. ratio=(ED$_{50}$ antagonist @ 3 mg/kg p.o.)/(ED$_{50}$ vehicle)

By calculating the ratio for all compounds at the same dose, i.e. 3 mg/kg p.o., a direct comparison can be made as to their effect at that dose. Thus the larger the ratio, the greater the difference between the ED$_{50}$ values following 5-HT$_{1A}$ antagonist and vehicle pretreatment, hence the greater the antagonist effect. In summary the greater the ratio the more potent the 5-HT$_{1A}$ antagonist is following oral administration.

Those compounds of EP-A-5 12755 which showed the best 5-HT$_{1A}$ affinity and 5-HT$_{1A}$/α$_1$ selectivity were tested for 5-HT$_{1A}$ antagonist activity (column 5) and those compounds which showed the best 5-HT$_{1A}$ antagonist activity (column 5) were further tested in the procedure of column 6. The results clearly show that compounds A1, A2 and A3 of the present invention showed good 5-HT$_{1A}$ binding affinity and 5-HT$_{1A}$/α$_1$ selectivity and showed a surprising increase in oral activity as 5-HT$_{1A}$ antagonists compared to the class of compounds disclosed generally in EP-A-512755. The oral 5-HT$_{1A}$-antagonist ratios for compounds A1, A2 and A3 (33.5, 23.4 and 34.4) should be compared with those of the respective analogous compounds of the prior art i.e. Examples 55, 60 and Example 3 (ratios, respectively of 3.2, 7.4 and 4.2).

The compounds of the invention can be prepared by known methods from known starting materials or starting materials that may be prepared by conventional methods. For example the compounds may be prepared by the general methods disclosed in EP-A-0512755.

One method of preparing the compounds of the invention comprises acylating an amine of formula

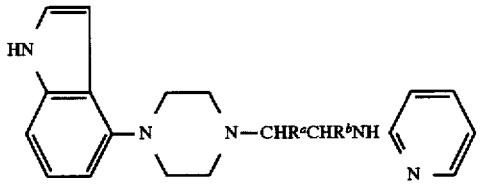

(B)

(where R$^a$ and R$^b$ are as defined above) with cyclohexanecarboxylic acid or an acylating derivative thereof. Examples of acylating derivatives include the acid halides (e.g. acid chlorides), azides, anhydrides, imidazolides (e.g. obtained from carbonyldiimidazole), activated esters or O-acyl ureas obtained from a carbodiimide such as a dialkylcarbodiimide particularly cyclohexylcarbodiimide.

The starting amides of general formula (B) are novel compounds and are also provided by the present invention. Some may be prepared by the general route disclosed in EP-A-0512755 e.g. the route exemplified below:

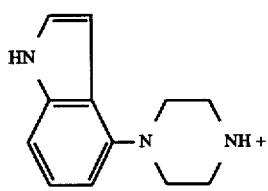

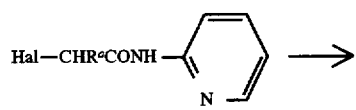

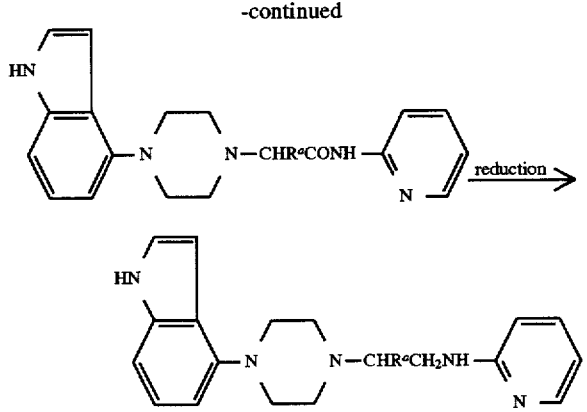

(where $R^a$ is as defined above and Hal is halo, particularly chloro or bromo). The reduction may be carried out with, for example a complex metal hydride, e.g. lithium aluminium hydride.

In an alternate method of preparing the starting materials of formula B the oxathiazolidine-2,2-dioxide of formula

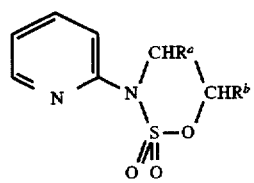

(where $R^a$ and $R^b$ are as defined above) is reacted with 4-piperazino indole. The reaction and a process for the preparation of the sulphoxide are illustrated in the scheme below:

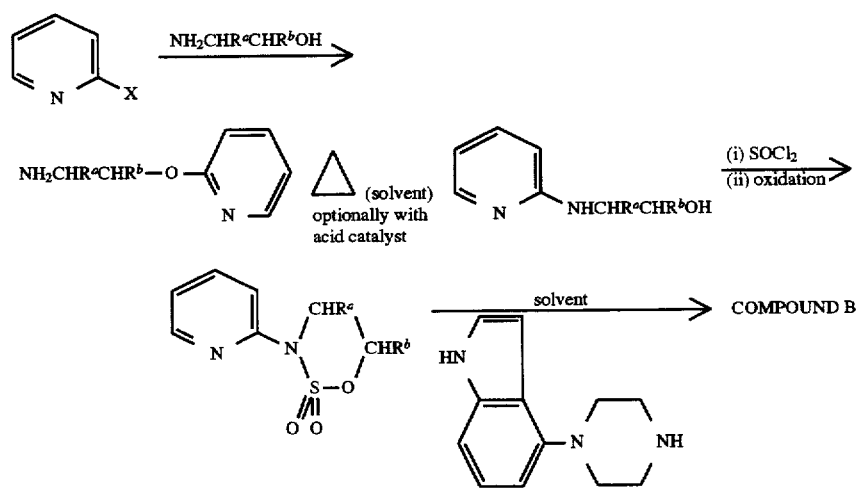

(where $R^a$ and $R^b$ are as defined above and X is a leaving group, preferably chloro, bormo or fluoro).

Certain process steps in the above scheme and certain novel intermediates of the scheme are claimed in our co-pending application entitled "Novel Processes and Intermediates for the Preparation of Piperazine Derivatives". This co-pending application has the same Applicants as the present application and claims priority from British patent application No. 9411108.5 filed on 3 Jun. 1994.

A further method of preparing the compounds of the invention comprises alkylating the amide of formula

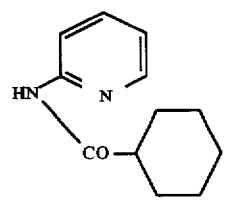

with an alkylating agent providing the group

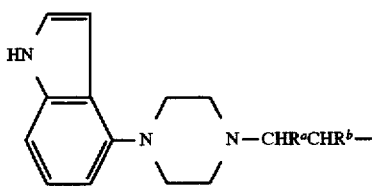

The alkylating agent may be, for example, a compound of formula

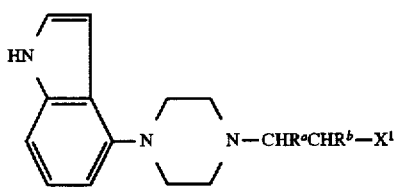

where $R^a$ and $R^b$ are as defined above and $X^1$ is a leaving group such as halogen or an alkyl- or aryl-sulphonyloxy group.

A further method of preparing the compounds of the invention comprises alkylating a compound of formula

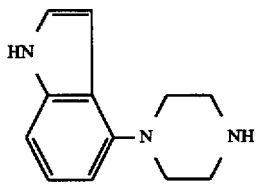

(C)

with a compound of formula

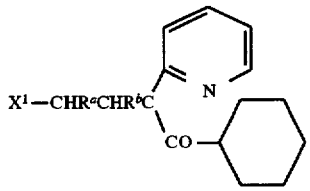

(where $R^a$, $R^b$ and $X^1$ are as defined above).

A further method of preparing the compounds of the invention comprises reacting a $N_{ind}$-protected derivative of a compound of formula

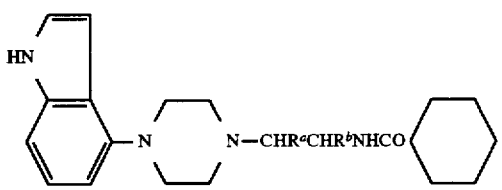

with 2-fluoropyridine N-oxide and subsequently removing the protecting group and the N-oxide group. The reaction may be carried out in the presence of a strong non-nucleophilic base (e.g. lithium diisopropylamide). The indole nitrogen may be protected with for example a benzoyl or benzyl group which can them be removed by mild hydrolysis or hydrogenolysis. The N-oxide group may be removed e.g. by tributyl tin hydride.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention may contain one or more asymmetric carbon atoms, so that some compounds can exist in different steroisomeric forms. The compounds can be, for example, racemates or optically active forms. The optically active forms can be obtained by resolution of the racemates or by asymmetric synthesis or using readily available chiral precursors e.g. R or S alaninol.

The invention also provides a pharmaceutical composition comprising a compound or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavoring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols, (e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged composition, for example picketed powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention.

EXAMPLE 1

(R)-N-(1-methyl-2-(4-indolyl-1-piperazinylethyl)-N-(2-pyridyl)cyclohexanecarboxamide (a) 4-Piperazinoindole 4-Aminoindole hydrochloride (89.4 g, 0.53 mole) bis-chloroethylamine HCl (94.5 g, 0.53 mole) and diisopropylethylamine (185 ml, 1.03 mole) were stirred and heated under reflux in chlorobenzene (1 L) under argon for 3 h. Diisopropylethylamine (92.5 ml, 68.5 g, 0.5 mole) was then added slowly over 1 h. The mixture was heated under reflux for a further 1 h and left at room temperature over night. The resulting gum was dissolved in isopropanol (500 ml). After evaporation to dryness the product was re evaporated with toluene to leave a black gum. After tritration with a mixture of ethylacetate/isopropanol the solid was filtered and washed with methanol affording 90 g of crude 4-piperazinoindole hydrochloride as a slate grey powder.

The grey powder was dissolved in water (1 L), made basic with sodium hydroxide solution then extracted with dichloromethane/methanol (3 L of $CH_2Cl_2$:MeOH 10:1). After the organic layer was washed with water, it was dried ($MgSO_4$) and evaporated under reduced pressure to leave a grey solid. The solid was triturated with isopropanol/ethylacetate and filtered to give 40 g of a pale grey solid.

(b) (R)-N-(2-pyridyl)-2-aminopropanol (R)-Alaninol (107.3 g, 1.43M) was added dropwise with stirring to a solution of potassium tertiary butoxide (160 g, 1.43M) in tetrahydrofuran (1 L). After the exothermic reaction had cooled to room temperature, 2-chloropyridine (162.4 g, 1.43M) was added dropwise. The reaction mixture was heated under reflux overnight, cooled, filtered and evaporated to an oil. The oil was dissolved in xylene (1.5 L) and toluene-p-sulphonic acid (0.5 g) was added. The mixture was heated under reflux overnight. On cooling to room temperature the product crystallised to give (R)-(R)-N-(2-pyridyl)-2-aminopropanol (190 g), $[\alpha]_D^{26}=30°$ (ca 1 in $CHCl_3$).

(c) (R)-4-methyl-3-pyrid-2-yl[1,2,3]-oxathiazolidine-2-oxide

A solution of (R)-N-(2-pyridyl)-2-aminopropanol (20.0 g, 0.13 moles) and N,N-diisopropylethylamine (33.6 g, 0.13 moles) in dichloromethane (500 ml) was cooled to 5° C. Then thionyl chloride (15.5 g, 0.13 moles) in dichloromethane (100 ml) was added slowly whilst the temperature was kept below 10° C. The mixture was stirred for 0.5 h. and ice cold water (500 ml) was added. The organic phase was separated and washed with water (5×500 ml). The aqueous phase was back-extracted with dichloromethane (2×500 ml), the organic phases were combined, dried ($MgSO_4$) and evaporated in vacuo to give a brown oil. This was purified on a silica column, eluting with diethyl ether to give (R)-4-methyl-3-(2-pyridyl)-[1,2,3] oxathiazolidine 2-oxide (154.4 g) as a clear oil.

(d) (R)-4-methyl-3-(2-pyridyl)-2-yl-[1,2,3] oxathiazolidine-2,2-dioxide

A solution of sodium periodate (21 g, 0.10 moles) in water (150 ml) was added slowly to a solution of (R)-4-methyl-3-pyridin-2-yl-[1,2,3]oxathiazolidine-2-oxide (15.4 g, 0.78 moles) and ruthenium(III)chloride (20 mg) in acetonitrile (1540 ml) whilst the temperature was kept below 5° C. A heavy precipitate developed. The mixture was poured into a mixture of ethyl acetate (500 ml) and water (500 ml) and then shaken. The organic phase was retained and the aqueous phase was extracted with further ethyl acetate (2×500 ml). The organic phases were combined, backwashed with water (500 ml), dried ($MgSO_4$) and then evaporated in vacuo to give (R)-4-methyl-3-(2-pyridyl)-[1,2,3]oxathiazolidine-2, 2-dioxide (15.5 g) as a yellow oil which solidified on standing.

(e) (R)-1-(4-indolyl)-4-[2-methyl-2-(2-pyridylamino) ethyl]piperazine

A solution of (R)-4-methyl-3-pyridin-2-yl-[1,2,3]-oxathiazolidine-2,2-dioxide (4.04 g 0.019 moles) and 4-piperazinoindole (3.80 g 0.019 moles) in acetonitrile (200 ml) was heated to 60° C. for 0.5 h then evaporated in vacuo. The residue was taken up into dilute HCl (100 ml), warmed to 60° C. for 0.5 h, cooled, washed with ethyl acetate (2×100 ml), made basic with potassium carbonate, extracted into dichloromethane (3×100 ml), dried ($MgSO_4$) then evaporated in vacuo to give a brown glass. This was purified on a silica column eluting with 10% propan-2-ol in dichloromethane to give (R)-1-(4-indolyl)-4-[2-methyl-2-(2-pyridinylamino)ethyl]piperazine (4.3 g) as a clear glass.

(f) (R)-N-(1-methyl-2-(4-indolyl-1-piperazinylethyl)-N-(2-pyridyl)cyclohexanecarboxamide A solution of (R)-1-(4-indolyl)-4-[2-methyl-2-(2-pyridylamino)ethyl piperazine (4.3 g 0.012 moles), triethylamine (2.47 g 0.024 moles) and cyclohexanecarbonyl chloride (1.8 g 0.012 moles) in dichloromethane (100 ml) was warmed to 60° C. for 0.5 h then evaporated in vacuo. The residue was taken up into dilute HCl (100 ml), washed with ethyl acetate (3×100 ml) made basic with potassium carbonate, extracted into dichloromethane (3×100 ml), backwashed with water (100 ml), dried ($MgSO_4$), then evaporated in vacuo to give (R)-N-(1-methyl-(4-indolyl-1-piperazinyl)ethyl-N-(2-pyridyl)cyclohexane carboxamide (4.3 g 80%) as a pale pink crystalline solid. The product was dissolved in methanol then treated with one mole equivalent of dilute hydrochloric acid. After evaporation to dryness and re-evaporation with isopropanol the product crystallised from IPA/$Et_2O$ as the monohydrochloride, white microcrystals mp 154°–156.5° C. Found: C:67.0; H:7.6; N14.4% $C_{27}H_{35}N_5O.HCl$ requires: C:67.3; H:7.5; N:14.7%.

EXAMPLE 2

(R)-N-(2-methyl-(4-indolyl-1-piperazinyl)ethyl-N-2-(pyridyl)cyclohexanecarboxamide (a) (S)-N-(2-pyridyl)-1-amino-2-propanol (S)-1-amino-2-propanol (43 g, 0.57M) was added to a stirred solution of potassium tertiary butoxide (64.2 g, 0.66M) in tetrahydrofuran (500 ml). 2-Chloropyridine (65.1 g 0.66M) was then added dropwise. After the exothermic reaction had subsided, the reaction was heated under reflux overnight, filtered to remove the potassium chloride and evaporated to an oil. The crude oil was dissolved in xylene (500 ml) and toluene-p-sulphonic acid (2 g) added and heated overnight under reflux under argon. After cooling to room temperature, the mixture was extracted with 2M hydrochloric acid. The acid extracts were basified with 2M sodium hydroxide and extracted into ethyl acetate. The ethyl acetate extracts were dried (MgSO$_4$) and after removal of the acetic acid the product was distilled affording 73.5 g of the title compound, bp 100°–110° C. at 0.2 mbar.

(b) (S)-4,5-Dihydro-5-dimethyl-3-(2-pyridyl)-3H-[1,2,3] oxathiazole-2-oxide

Thionylchloride (8.8 ml, 14.35 g 0.12M) in dichloromethane (20 ml) was added dropwise to a cooled stirred solution of (S)-N-(2-pyridinyl)-1-amino-2-propanol (18.28 g, 0.12M) in dichloromethane (180 ml) and diisopropylethylamine (31 g, 0.24M) keeping the temperature below 5° C. After stirring at 0° for 1 h a solution of saturated sodium bicarbonate solution was added keeping the temperature below 5° C. The organic layer was separated, dried (Na$_2$SO$_4$) and concentrated to give 27.6 g of a yellow oil. The oil was chromatographed on silica using 40% ethylacetate in hexane to give 20.28 g of a yellow oil containing a 4:3 mixture of diastereoisomers.

(c) (S)-4,5-Dihydro-5-methyl-3-(2-pyridyl)-3H-[1,2,3] oxathiadiazole-2,2-dioxide A solution of sodium periodate (27.3 g 0.13M) in water (200 ml) was added with stirring to (S)-4,5-dihydro-5-methyl-3-(2-pyridinyl)-3H-[1,2,3]oxathiadiazole-2-oxide (20.23 g, 0.1M) in acetonitrile containing ruthenium III chloride (21 mg, 0.1 mmole, 0.1 mole %) at −10°–0° C. over a period of 25 minutes. After stirring at 0° for 1 h, at room temperature for 2 h, the reaction mixture was added to water (800 ml) and extracted with ethylacetate (2×200 ml) dried (Na$_2$SO$_4$) and evaporated to an oil under reduced pressure (temperature <30° C.). Trituration with acetonitrile gave an off-white solid, 14.86 g, mp 99°–100° C. (decomp) $[\alpha]_D^{27}$+ 28° [ca 1 in CHCl$_3$). Found: C,44.9; H,4.65; N,.13.0% C$_8$H$_{10}$N$_2$O$_3$S requires C, 44.85; H, 4.7; N, 13.1%.

(d) (R)-1-(4-indolyl)-4-[2-methyl-2-(2-pyridylaminoethyl)piperazine

A mixture of (S)-4,5-dihydro-5-methyl-3-(2-pyridinyl)-3H(1,2,3)oxathiazole-2,2-dioxide (2.02 g, 9.5 mM), 4-piperazinoindole (1.9 g, 9.5 mM) in acetonitrile (100 ml) was stirred and heated for 1 h. The solvent was removed under reduced pressure and the residue dissolved in dilute hydrochloric acid. The solution was heated to 60° C. for 10 m and then washed with CH$_2$Cl$_2$ (100 ml). The solution was basified (K$_2$CO$_3$) to give a black solid which was extracted with dichloromethane (2×100 ml) containing some methanol. The remaining solid was filtered, the organic fraction washed with water, dried (MgSO$_4$) and evaporated to a dark brown material 2.5 g. The oil was dissolved in methanol and treated with a solution of hydrogen chloride in dry ether affording a white precipitate of the hydrochloride mp 125°–130° C., $[\alpha]_D^{24}$ −16° [ca 1 in MeOH]. Found: C, 53.9; H, 6.75; N, 15.5%. C$_{20}$H$_{25}$NS 2HCl.2H$_2$O requires C, 54.0; N, 7.0; N, 15.8%.

(e) (R)-N-(2-methyl-(4-indolyl-1-piperazinyl)ethyl-N-(2-pyridyl)cyclohexane carboxamide Cyclohexane carboxylic acid chloride (0.53 g, 3.6 mM) in dichloromethane (20 ml) was added dropwise to a stirred solution of the amine obtained in Example 2(d) (1.26 g, 3.6 mM) and triethylamine in dichloromethane (20 ml). After heating to 50° for 20 m, and removal of the solvent, the residue was taken up in dilute hydrochloric acid. After filtering the solution was basified (K$_2$CO$_3$) and extracted with dichloromethane. After drying (MgSO$_4$) the solvent was removed to give a brown glass which was dissolved in ethylacetate and a solution of hydrogen chloride in dry ether added affording 1.5 g of the title compound as the hydrochloride, mp 125°–130° as a white powder, $[\alpha]_D^{24}$+ 25° [ca 1 in MeOH]. Found: C, 63.6; H, 7.4; N, 13.6. C$_{27}$H$_{35}$N$_5$O 1.5H$_2$O requires C, 63.7; N, 7.4; N, 13.8%.

EXAMPLE 3

N-[2-(4-(4-Indolyl)-1-piperazinyl)ethyl]-N-(2-pyridyl)cyclohexanecarboxamide (a) 2-Chloro-N-(2-pyridinyl)acetamide Chloroacetylchloride (60 g, 0.53M) was added with stirring to a mixture of 2-aminopyridine (50 g, 0.53M) and diisopropylethylamine (75 ml, 0.53M) in dichloromethane (500 ml) keeping the temperature below 5° C. After the reaction mixture was warmed to room temperature it was filtered and washed with water. The organic layer was dried (MgSO$_4$) and evaporated under reduced pressure to give 72.6 g of a brown solid.

(b) 2-(1-(4-(4-indolyl)piperazinyl))-N-(2-pyridyl) acetamide

The chloroacetamide obtained above (8.9 g, 52 mM), 4-piperazino indole (10 g, 49 mM) and diisopropylethylamine (8.6 ml, 50 mM) were dissolved in DMF (30 ml) and heated to 60° C. under argon. After 2 h the mixture was cooled, poured into water and extracted with ethylacetate. The combine organic extracts were then extracted with hydrochloric acid (2M). The combined acid extracts were basified (NaHCO$_3$) and extracted into ethylacetate. After washing with water the organic phase was dried (MgSO$_4$) and evaporated under reduced pressure to give 7.63 g. This was chromatographed on silica eluting with ethylacetate hexane (1:2) to give 7.34 g of a yellow oil.

(c) 1-(4-Indolyl)-4-[2-(2-pyridylamino)ethyl]piperazine

The product from Example 3(b) above (4.88 g, 13.4 mM) was dissolved in dry tetrahydrofuran (200 ml) under argon and lithium aluminium hydride (2.03 g, 53.3 mM) added portionwise with stirring. After heating under reflux for 20 min, water (2 ml), sodium hydroxide (15% aq., 2 ml) and water (6 ml) were added sequentially. The resulting precipitate was filtered and washed with ethyl acetate. After evaporating, the oil remaining was redissolved in ethylacetate, washed with water and dried (MgSO$_4$). After removal of the solvent 4.12 g of oil remained. The oil was recrystallised from ethylacetate hexane mixture to give 2.64 g of solid.

1.36 g of the solid was dissolved in dichloromethane and the hydrochloride precipitated with ethereal hydrochloric acid to give 1.52 g of white solid mp 153°–60° C. (Found C, 53.9; H, 6.5; N, 16.2%. C$_{19}$H$_{23}$N$_5$ 2.5HCl, 0.75H$_2$O Requires: C, 53.6, H, 6.4; N, 16.4%.)

d) N-[2-(4-(4-Indolyl)-1-piperazinyl)ethyl]-N-(2-pyridyl) cyclohexanecarboxamide The amine from Example 3(c) above, (2.33 g, 7.24 mM) in dichloromethane (20 ml) and triethylamine (1 ml, 7.3 mM) under argon was treated at 0° C. with stirring with a solution of cyclohexane carbonyl chloride (0.97 ml, 7.3 mM) in dichloromethane (2 ml). After 2 h a further portion (0.1 ml) of the acid chloride was added and after a further 15 min the reaction was complete. The reaction mixture was evaporated to an oil, dissolved in ethyl acetate and washed with water and saturated sodium bicarbonate solution. After drying (MgSO$_4$), removal of the solvents left an oil, which was chromatographed on silica eluting with diethyl ether, affording 1.89 g of product which was converted to the hydrochloride salt by solution in dichloromethane and precipitation of the salt with ethereal hydrogen chloride to give 1.88 g of a white solid, mp 181°–187°. Found: C, 63.6; H, 7.3; N, 14.05%. C$_{26}$H$_{33}$N$_5$O HCl 1.25H$_2$O requires C, 63.7; H, 7.5; N, 14.3%).

We claim:

1. A compound of the general formula A:

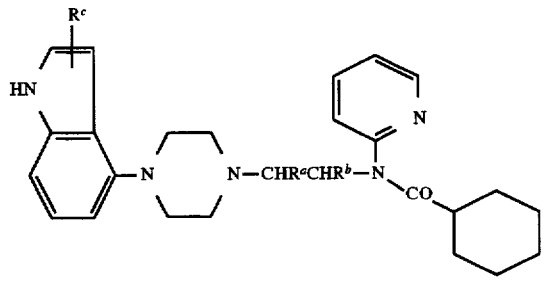

(A)

where R$^a$ and R$^b$ are each hydrogen or methyl and R$^c$ is hydrogen, halo or C$_{1-4}$ alkyl; or a pharmaceutically acceptable acid addition salt thereof.

2. A compound as claimed in claim 1 wherein R$^c$ is hydrogen.

3. (R)-N-(1-methyl-2-(4-indolyl-1-piperazinyl)ethyl-N-(2-pyridyl)cyclohexanecarboxamide or a pharmaceutically acceptable acid addition salt thereof.

4. (R)-N-(2-methyl-(4-indolyl-1-piperazinyl)ethyl)-N-(2-(pyridyl)cyclohexanecaroxamide or a pharmaceutically acceptable acid addition salt thereof.

5. N-[2-(4-(4-Indolyl)-1-piperazinyl)ethyl]-N-(2-pyridyl)cyclohexanecarboxamide or a pharmaceutically acceptable acid addition salt thereof.

6. A pharmaceutical composition comprising a compound as claimed in claim 1 in combination with a pharmaceutically acceptable diluent or carrier.

7. A method of treating anxiety or depression in a mammal in need of such treatment which comprises administering to such mammal an amount effective to alleviate such condition of a compound having the formula

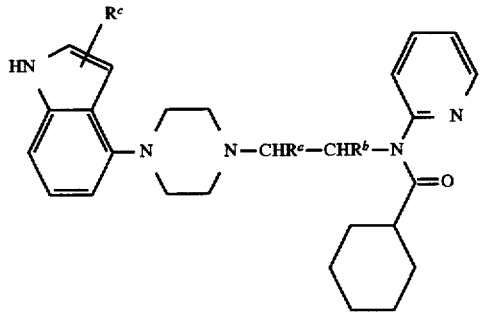

where R$^a$ and R$^b$ are each hydrogen or methyl and R$^c$ is hydrogen, halo or C$_{1-4}$ alkyl; or a pharmaceutically acceptable acid addition salt thereof.

8. A method of treatment according to claim 7 wherein the compound used is:

(R)-N-(1-methyl-2-(4-indolyl)-1-piperazinyl)ethyl)-N-(2-pyridyl)-cyclohexanecarboxamide, (R)-N-(2-methyl-2-(4-indolyl)-1-piperazinyl)ethyl)-N-(2-pyridyl)cyclohexanecarboxamide, or N-[2-(4-(4-indolyl)-1-piperazinyl)ethyl]-N-(2-pyridyl) cyclohexanecarboxamide.

9. An amine of formula B:

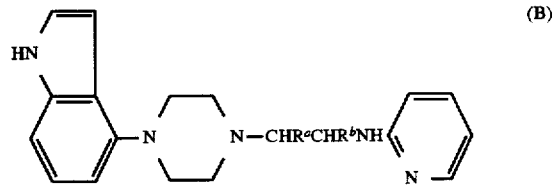

(B)

where R$^a$ and R$^b$ are each hydrogen or methyl.

10. A method of preparing a compound as claimed in claim 1 comprising acylating an amine of formula B:

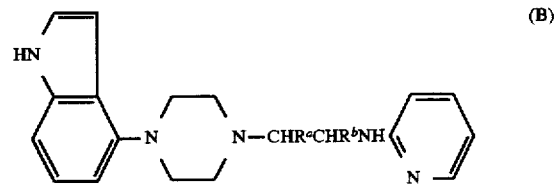

(B)

(where R$^a$ and R$^b$ are each hydrogen or methyl) with cyclohexanecarboxylic acid or an acylating derivative thereof.

11. A method of preparing a compound as claimed in claim 1 comprising alkylating an amide of formula:

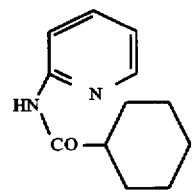

with an alkylating agent of formula:

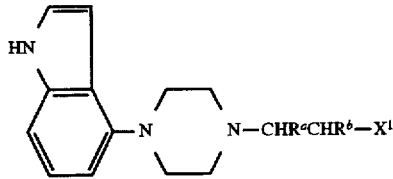

wherein R$^a$ and R$^b$ are each hydrogen or methyl and X$^1$ is a leaving group.

12. A method of preparing a compound as claimed in claim 1 comprising alkylating a compound of formula C:

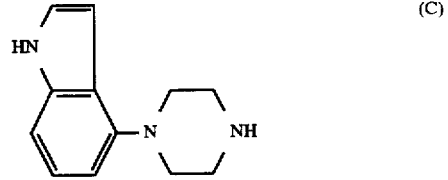

(C)

with a compound of formula
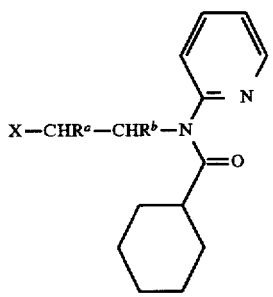
wherein $R^a$ and $R^b$ are each hydrogen or methyl and $X^1$ is a leaving group.
13. A method of preparing a compound as claimed in claim 1 comprising reacting a indole nitrogen protected derivative of a compound of formula
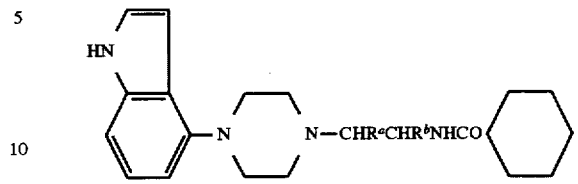
with 2-fluoropyridine N-oxide and subsequently removing the protecting group and the N-oxide group.
* * * * *